United States Patent [19]

Langley

[11] 3,997,601

[45] Dec. 14, 1976

[54] ADIPIC ACID MANUFACTURE

[75] Inventor: Philip Edward Langley, Stockton-on-Tees, England

[73] Assignee: Imperial Chemical Industries Limited, London, England

[22] Filed: Aug. 5, 1974

[21] Appl. No.: 495,041

[30] Foreign Application Priority Data

Aug. 20, 1973  United Kingdom ............ 39223/73

[52] U.S. Cl. .................... 260/531 R; 260/537 P
[51] Int. Cl.² ........................................ C07C 51/28
[58] Field of Search ................... 260/537 P, 531 R

[56] References Cited

UNITED STATES PATENTS

| | | | |
|---|---|---|---|
| 3,673,245 | 6/1972 | Mims | 26/531 R |
| 3,761,517 | 9/1973 | Rohl | 260/531 R |
| 3,880,921 | 4/1975 | Hellemanns et al. | 260/531 R |

*Primary Examiner*—Vivian Garner
*Attorney, Agent, or Firm*—Cushman, Darby & Cushman

[57] ABSTRACT

In the continuous manufacture of adipic acid by nitric acid oxidation of an organic feedstock oxidisable thereto in which cooling is effected by recycling the reaction mixture through a cooling circuit external to the reactor, improved temperature control is achieved by feeding the feedstock to the cooling circuit upstream of at least one cooler.

6 Claims, No Drawings

ADIPIC ACID MANUFACTURE

This invention relates to the manufacture of adipic acid, more particularly, to the manufacture of adipic acid by the nitric acid oxidation of an organic feedstock oxidizable thereto.

Adipic acid is commonly made by the nitric acid oxidation of cyclohexanol or cyclohexanone, mixtures thereof, or mixtures containing either or both of them and possibly other materials oxidizable to adipic acid. The usual starting material is the product of the air oxidation of cyclohexane consisting principally of a mixture of cyclohexanol and cyclohexanone and frequently known as 'KA'. The oxidation may be carried out in the presence of a metallic catalyst, for example a manganese, copper or vanadium catalyst, a mixture of copper and vanadium being particularly suitable. In commercial operation the organic feedstock, for example KA, and the nitric acid, usually containing a metallic catalyst, are fed continuously to a reaction vessel. To isolate the product an effluent stream from the reactor is cooled and the adipic acid which crystallizes is separated, the mother liquor being recycled to the reactor after bringing the nitric acid up to its original strength.

It is desirable to keep the reaction mixture in the reactor at a temperature within the range 70° to 90° C. At lower temperatures solid acid tends to crystallize while, at higher temperatures, the yield of adipic acid is reduced and the proportion of by-products increased.

The reaction is, however, highly exothermic leading to difficulties in temperature control. Because of this it is the usual practice to recycle at least a part of the reaction mixture in the reaction vessel through a cooling circuit which is external to the vessel.

We have now found, surprisingly, that where an external cooling circuit is used more effective temperature control is achieved if at least a part of the organic feedstock is fed to the cooling circuit upstream of a cooler instead of to the reaction vessel. By this means the rate at which the organic feedstock can be fed to the process without the desired upper limits of temperature being transgressed is increased, with obvious economic advantages.

Accordingly our invention provides a continuous process for the manufacture of adipic acid by oxidizing an organic feedstock oxidizable to adipic acid with nitric acid in a reaction vessel and controlling the temperature of the reaction mixture by recycling at least a part of it through a cooling circuit which is external to the reaction vessel and contains at least one cooler, in which process at least a part of the organic feedstock is fed to the cooling circuit upstream of at least one cooler.

As the organic feedstock there may be used any organic compound or mixture of compounds which is oxidizable to adipic acid with nitric acid. Cyclohexanol and cyclohexanone are especially important, and particularly the product of the air oxidation of cyclohexane consisting principally of a mixture of these two compounds and usually known as KA.

The nitric acid may vary in concentration, for example from 30 to 60% by weight, and preferably from 45 to 55% by weight. The nitric acid is usually made up in part of recovered nitric acid from which the product adipic acid has been separated and in part of fresh nitric acid added to maintain the desired concentration. The recovered nitric acid contains a proportion of adipic acid in solution, and usually also certain impurities, notably glutaric acid and succinic acid, formed in the oxidation of the feedstock. In order to maintain the concentration of these impurities in the nitric acid at an acceptable level a proportion of the recovered nitric acid may be taken as a purge. Preferably the nitric acid is fed directly to the reaction vessel.

The temperature of the reaction mixture in the reaction vessel is desirably kept between the limits of 70° to 90° C, and preferably between the limits of 73° and 75° C. To control the temperature at least a part of the reaction mixture is recycled, external to the reaction vessel, through a cooling circuit containing at least one cooler. This does not, of course, preclude the use of supplementary means of cooling such as cooling coils inside the reaction vessel, although these must be used with care because of the risk of solid acid being deposited on them, so reducing their effectiveness, and indeed the effectiveness of internal cooling coils is limited by this factor.

Although the process of our invention may be carried out under pressure if desired, for example at pressures up to 50 atmospheres, it is an advantage of our process that it may be carried out at atmospheric pressure or at the pressures slightly above atmospheric caused by gas evolution from the reaction mixture, for example up to 5 lbs. per square inch (gauge).

The degree of recycle through the cooling circuit is usually high: thus the rate at which reaction mixture is recycled is usually several times, for example from 2 to 10 times, the rate at which fresh reactants are fed to the reactor or cooling circuit.

The cooler in the cooling circuit may be of any convenient type, for example a vessel comprising a number of tubes, through which the reactant mixture is passed, contained in a shell through which coolant, usually water, is circulated. More than one cooler may be used if desired.

The organic feedstock is fed, at least in part, to the cooling circuit upstream of at least one cooler. Preferably the whole of the organic feedstock is fed to the cooling circuit, and preferably also it is fed upstream of all the coolers where more than one cooler is used.

If desired, the reaction mixture leaving the reactor may be passed to a further reactor or series of reactors in which further reaction takes place, and to which, if desired, more organic feedstock may be fed.

Compared with a process operated in a reactor with an external cooling circuit as hereinbefore described in which the organic feed and nitric acid are fed to the reactor, the process of the present invention, operated in an identical reactor and cooling circuit, but in which the organic feed is fed to the cooling circuit upstream of the coolers while the nitric acid is fed to the reactor, enables a lower temperature to be achieved in the reactor at the same feed rate, for example a temperature of 74° C as against 80° C, with improvement in the yield and quality of the adipic acid. If the same temperature is maintained as in the prior process the feed rate can be increased by up to as much as 50%.

It is surprising that the efficiency of the reaction can be influenced by the point of introduction of the KA. Without wishing to be limited by theory, we nevertheless believe that the initial reaction step in the oxidation of KA to adipic acid is the formation of an intermediate adiponitrolic acid. This reaction step is very rapid and leads to release of more than 80% of the overall heat of the reaction. The other reaction steps are relatively slower and less exothermic. This theory is consistent with our discovery that it is important to introduce at least part of the KA into the nitric acid at a point where cooling is a maximum in order to limit the temperature rise and so achieve good rates of throughput with good quality product.

Our invention is illustrated but not limited by the following Examples.

EXAMPLE 1

The reactor consisted of a vertical reactor fitted with an external circuit through which the reaction mixture could be pumped through a cooler in the circuit. Nitric acid of 55% by weight concentration was fed to the bottom of the reactor and a KA obtained by the oxidation of cyclohexane and comprising 90% by weight of cyclohexanol and 7% by weight of cyclohexanone was fed to the external circuit upstream of the cooler. A degree of recycle of 9:1 through the external circuit was established. At a constant feed rate of KA and nitric acid the temperature in the reactor was 78° C.

The experiment was repeated under identical conditions except that the KA was fed directly to the reactor with the nitric acid. The temperature in the reactor was 84° C and the yield of adipic acid was reduced by 0.8%.

EXAMPLE 2

The procedure of Example 1 was repeated feeding the same KA to the external circuit upstream of the cooler but at a lower feed rate. The temperature in the reactor was 75° C.

The experiment was repeated under identical conditions except that the KA was fed directly to the reactor with the nitric acid at the same lower feed rate. The temperature in the reactor was 81° C and the yield of adipic acid was reduced by 0.8%.

EXAMPLE 3

The procedure of Example 1 was repeated except that the feed rate of the KA was increased until the temperature in the reactor under steady conditions was 81° C. An increase in feed rate of 20% was thereby achieved.

I claim:
1. In a continuous process for the manufacture of adipic acid by the oxidation with nitric acid of an organic feedstock consisting essentially of cyclohexanol, cyclohexanone or mixtures thereof, the improvement which consists essentially of:
   a. oxidizing the reaction mixture of organic feedstock with nitric acid at a temperature of 70° to 90° C in a reaction vessel;
   b. controlling the temperature of the reaction mixture in said reaction vessel between 70° and 90° C by recycling the reaction mixture through a cooling circuit external to the reaction vessel and containing at least one cooler;
   c. feeding nitric acid to the reaction vessel; and
   d. feeding at least a part of the organic feedstock to the cooling circuit upstream of at least one cooler, the recycle rate of the reaction mixture being at least twice the rate at which fresh reactants are fed, whereby adipic acid is formed without crystallisation of adipic acid in the reactor.

2. A process according to claim 1 wherein the recycle rate is from 2 to 10 times the rate at which fresh reactants are fed.

3. A process as claimed in claim 1 in which the organic feedstock is the product of the air oxidation of cyclohexane.

4. A process as claimed in claim 1 in which the concentration of the nitric acid is in the range 30 to 60% by weight.

5. A process as claimed in claim 1 in which the whole of the organic feedstock is fed to the cooling circuit.

6. A process as claimed in claim 5 wherein more than one cooler is used and in which the organic feedstock is fed to the cooling circuit upstream of all of the coolers.

* * * * *